United States Patent

Joerg et al.

Patent Number: 5,151,541
Date of Patent: Sep. 29, 1992

[54] PROCESS FOR THE PREPARATION OF DIALKYL CARBONATES

[75] Inventors: Klaus Joerg, Limburgerhof; Rudolf Kummer, Frankenthal; Franz-Josef Mueller, Wachenheim, all of Fed. Rep. of Germany

[73] Assignee: BASF Aktiengesellschaft, Ludwigshafen, Fed. Rep. of Germany

[21] Appl. No.: 562,708

[22] Filed: Aug. 6, 1990

[30] Foreign Application Priority Data

Aug. 12, 1989 [DE] Fed. Rep. of Germany ....... 3926710

[51] Int. Cl.⁵ .............................................. C07C 69/96
[52] U.S. Cl. ........................................................ 558/277
[58] Field of Search .......................................... 558/277

[56] References Cited

U.S. PATENT DOCUMENTS

| Re. 29,338 | 8/1977 | Perotti et al. | 558/26 |
| 3,846,468 | 0/1974 | Perotti et al. | 558/26 |
| 3,952,045 | 4/1976 | Gaenzler et al. | 558/26 |
| 4,218,391 | 8/1980 | Romano et al. | 558/26 |
| 4,370,275 | 1/1983 | Stammann et al. | 558/26 |
| 4,636,576 | 1/1987 | Bhattacharya et al. | 558/26 |
| 4,638,076 | 1/1987 | Bhattacharya | 558/26 |
| 4,761,467 | 8/1988 | Bhattacharya | 558/26 |

FOREIGN PATENT DOCUMENTS

| 2110194 | of 1971 | Fed. Rep. of Germany | 558/26 |
| 2334736 | of 1975 | Fed. Rep. of Germany | 558/26 |
| 2743690 | of 1978 | Fed. Rep. of Germany | 558/26 |
| 45-11129 | of 1970 | Japan | 558/26 |
| 60-252450 | 5/1984 | Japan | 558/260 |

OTHER PUBLICATIONS

Chem. Abstr. vol. 73 (1970) 14236a.
J. Org. Chem., vol. 35, No. 9 (1970) 2976-2978.

*Primary Examiner*—Mary C. Lee
*Assistant Examiner*—Robert C. Whittenbaugh
*Attorney, Agent, or Firm*—John H. Shurtleff

[57] ABSTRACT

A process for the preparation of dialkyl carbonates of the general formula I

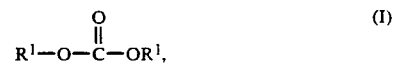

in which $R^1$ denotes $C_1$-$C_{10}$-alkyl, by reaction of alcohols $R^1OH$ with a gaseous carbon monoxide/oxygen mixture in the presence of a copper catalyst and a co-solvent at elevated temperature and pressure wherein the co-solvent used is a cyclic urea of the general formula II

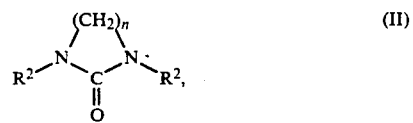

in which n is equal to 2, 3 or 4 and $R^2$ denotes hydrogen or $C_1$-$C_4$-alkyl.

10 Claims, No Drawings

PROCESS FOR THE PREPARATION OF DIALKYL CARBONATES

The present invention relates to a process for the preparation of dialkyl carbonates of the general formula I

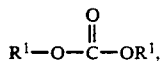

in which $R^1$ denotes $C_1$–$C_{10}$-alkyl, by reaction of alcohols $R^1OH$ with a gaseous carbon monoxide/oxygen mixture in the presence of a copper catalyst and a co-solvent at elevated temperature and pressure.

Saegusa et al [J. Chem. 35, 2976–2978, (1970)] describe the preparation of dimethyl carbonate from carbon monoxide, oxygen and methanol using copper(methoxy) chloride as catalyst.

According to JP-45/11,129 (1970), copper(II) halides are used for this purpose.

In DE-A 2,743,690, simple salts of monovalent copper are used for the preparation of dimethyl carbonate, whilst DE-A 2,110,194 prefers the use of copper complexes with nitrogenous heterocyclic compounds such as pyridine, dipyridyl or phenanthroline. Such nitrogenous heterocyclic compounds are also made use of in U.S. Pat. No. 4,761,467 together with copper(methoxy) chloride for the preparation of carbonates, whereas DE-A 2,334,736 claims the use of triarylphosphine oxides, organic phosphites, phosphates or phosphonates as complexing agents for copper in this reaction. Nitrogen bases as complexing agents for copper ions in the preparation of carbonates are the subject matter of U.S. Pat. No. 4,370,275.

A different method of solubilizing copper catalysts which are difficultyly soluble in an organic reaction medium is used in U.S. Pat. No. 4,636,576 and U.S. Pat. No. 4,638,076. Instead of the classical complexing agents, difficultly volatile co-solvents such as cyclic amides, for example N-methylpyrrolidone or caprolactam, or, respectively, phosphoric acid amides, for example hexamethylphosphoric acid triamide and tri(phentamethylene)phosphoric acid triamide are added to the reaction medium.

The fact that so many methods have been proposed for the preparation of dialkyl carbonates shows that the proposed solutions suffer from numerous drawbacks, such as unsatisfactory space-time yields, problems incurred in working up the reaction mixture, corrosion problems and problems arising from the use of toxic complexing agents or co-solvents. It is thus an object of the present invention to provide a process for the preparation of dialkyl carbonates which does not suffer from any of the drawbacks associated with the prior methods.

We have thus found a process for the preparation of dialkyl carbonates of the general formula I

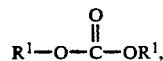

in which $R^1$ denotes $C_1$–$C_{10}$-alkyl, by reaction of an alcohol $R^1OH$ with a gaseous carbon monoxide/oxygen mixture in the presence of a copper catalyst and a co-solvent at elevated temperature and pressure, wherein the co-solvent used is a cyclic urea of the general formula II

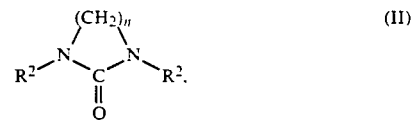

in which n is equal to 2, 3 or 4, and $R^2$ denotes hydrogen or $C_1$–$C_4$-alkyl.

The co-solvent used in the process of the invention is a cyclic urea of the general formula II in which n is equal to 2, 3 or 4 and $R^2$ denotes hydrogen or methyl, ethyl, propyl or butyl. The radicals $R^2$ may be the same or different and have a straight or branched chain. However, we prefer to use cyclic ureas in which the radicals $R^2$ are the same and denote straight-chain alkyl groups. A particularly preferred co-solvent is dimethylethylene urea (DMEAU) of formula III

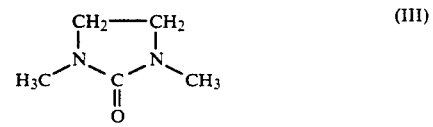

or dimethylpropylene urea (DMPU) of formula IV

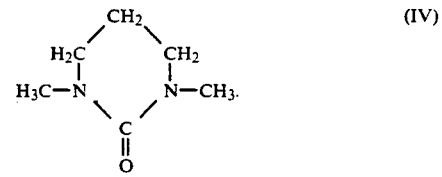

Mixtures of different cyclic ureas may, of course, also be used ass co-solvents.

To prepare the dialkyl carbonates I, according to the formula reaction equation (1):

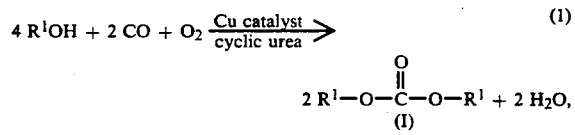

the alkanol to be converted is placed in the reactor together with the cyclic urea and the copper catalyst. In general, the molar ratio of alkanol to cyclic urea to copper salt will be 1:(0.1–1):(0.01–0.1), advantageously 1:(0.2–0.6):(0.03–0.07) and in particular 1:(0.4–0.5):(0.04–0.06).

In general, the process of the invention is used to convert $C_1$–$C_{10}$-alkanols to the corresponding dialkyl carbonates. The conversion of higher homologues is equally possible, although of no economical significance. The alcohols to be converted may be linear or branched. Preferably, the process of the invention is used for the conversion of $C_1$–$C_4$-alkanols to dialkyl carbonates and more preferably for the preparation of dimethyl and diethyl carbonates.

The copper catalyst used in process of the invention is, in general, a simple copper salt such as a copper halide, preferably a copper(I) halide, e.g. copper(I) chloride, copper(I) bromide or copper(I) iodide, copper sulfate or a copper(alkoxy) halide, e.g. copper(methoxy) chloride, copper(ethoxy) chloride, copper(propoxy) chloride, copper(butoxy) chloride or copper(methoxy) bromide. When use is made of a copper(alkoxy) halide as catalyst, it is advantageous to choose an alkoxy component which corresponds to the alkanol to be converted, as otherwise mixed dialkyl carbonates will result, which is not generally desirable.

Since the reaction represented by equation (1) is a redox reaction catalysed by the copper salt, an equilibrium between copper(I) and copper(II) salts occurs in the reaction mixture during the course of the reaction, regardless of whether a copper(I) halide or a copper(alkoxy) halide is used as starting catalyst.

To start the reaction, a gas mixture consisting of carbon monoxide and oxygen is bubbled through the reaction mixture. The proportions of the gaseous components may be varied within wide limits, but it is advantageous to operate with a gas mixture in which the oxygen content is sufficiently low to avoid the formation of explosive gas mixtures but sufficiently high to ensure a satisfactory conversion rate and, consequently, a good space-time yield. In general, a $CO/O_2$ molar ratio of from 1:0.05 to 1:0.15, preferably from 1:0.05 to 1:0.10 and more preferably from 1:0.06 to 1:0.08 is used (standardized to 1 mole of CO).

The reaction gases carbon monoxide and oxygen are bubbled into the liquid present in the reactor. To improve dispersion of said gases, the liquid reaction medium in the reactor may be additionally stirred by mechanical means. The type of reactor used is advantageously a bubbler reactor equipped with heating means and also, if desired, stirring means.

The reaction is advantageously carried out under elevated pressure, generally under a pressure of from 1 to 100 bar and preferably from 10 to 50 bar and more preferably from 20 to 30 bar. The reaction temperature is generally from 70° to 150° C., advantageously from 80° to 130° C. and preferably from 90° to 120° C.

The reaction may be carried out continuously or batchwise. In continuous operation, the reaction gases are passed through the reaction medium at such a rate that the unreacted carbon monoxide/oxygen off-gas continuously entrains the dialkyl carbonate formed together with the water of reaction and together with sufficient alkanol for the continuous formation of a low-boiling ternary azeotrope. This effect is generally achieved by bubbling the $CO/O_2$ gas mixture through the liquid reaction medium at a rate of from 10 to 50, advantageously from 15 to 35 and preferably from 20 to 30, liters (STP) per g of copper present in the reactor in the form of copper catalyst, per hour. Under these conditions, the copper catalyst and the co-solvent remain in the reactor.

The gaseous effluent is then separated in a condenser into its gaseous (STP) components, i.e. carbon monoxide and oxygen, and its liquid (STP) components, i.e. dialkyl carbonate, water of reaction and alkanol. It is advantageous to recycle the off-gas, duly replenished with carbon monoxide and oxygen, to the reaction. The liquid portions removed from the separator are distilled, the dialkyl carbonate being isolated, whilst the alkanol is recycled to the reactor, if desired.

In a batchwise operation of the process of the invention, it is possible to obtain dimethyl carbonate yields in the range of 80-90%.

EXAMPLES

Example 1

105 g of anhydrous methanol, 14.0 g of CuOMeCl (0.11 mole) and 40 g of DMPU (dimethylpropylene urea, b.p. 246° C.) were placed in a corrosion-resistant autoclave having a capacity of 0.3 liter and caused to react under a CO pressure of 35 bar for 30 minutes at 90° C. The pressure was let down and the reaction mixture cooled and analyzed by gas chromatography. It contained up to 90% of dimethyl carbonate (based on Cu salt used), and the selectivity was 99%.

Example 2

105 g of anhydrous methanol, 10.5 g of CuCl (0.11 mole) and 40 g of DMEU (dimethylethylene urea, b.p. 225° C.) were reacted under an $O_2$ pressure of 8 bar for 15 minutes at 90° C. The $O_2$ was then replaced by CO, and the methanol was converted to dimethyl carbonate (DMC) under a pressure of 35 bar over a period of 30 minutes. The yield of DMC was 76% (based on Cu salt used), as determined by GC analysis.

We claim:

1. In a process for the preparation of a dialkyl carbonate of the formula

in which $R^1$ is $C_1$–$C_{10}$-alkyl, by reaction of an alcohol $R^1OH$ with a gaseous carbon monoxide/oxygen mixture in the presence of a copper catalyst and a co-solvent at an elevated temperature of about 70° to 150° C. and under pressure of about 1 to 100 bar, the improvement which comprises:

using as the co-solvent at least one cyclic urea of the formula

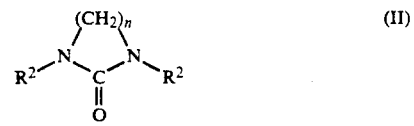

in which n is equal to 2, 3 or 4 and $R^2$ denotes hydrogen or $C_1$–$C_4$-alkyl.

2. A process as claimed in claim 1, wherein the copper catalyst used is copper(methoxy) chloride or copper(methoxy) bromide.

3. A process as claimed in claim 1, wherein the copper catalyst used is copper(I) chloride or copper(I) bromide.

4. A process as claimed in claim 1, wherein the co-solvent used is dimethylethylene urea and/or dimethylpropylene urea.

5. A process as claimed in claim 1, wherein the reaction is carried out at a temperature of from 80° to 130° C. and under a pressure of from 10 to 50 bar.

6. A process as claimed in claim 1, wherein the reaction is carried out at a temperature of from 90° to 120° C. and under a pressure of from 20 to 30 bar.

7. A process as claimed in claim 1, wherein $R^1$ in the formula (I) and the alcohol $R^1OH$ is methyl or ethyl.

8. A process as claimed in claim 1, wherein the molar ratio of alkanol to cyclic urea to a copper salt catalyst is 1:(0.1–1):(0.01–0.1).

9. A process as claimed in claim 1, wherein the molar ratio of alkanol to cyclic urea to a copper salt catalyst is 1:(b 0.2–0.6):(0.03–0.07).

10. A process as claimed in claim 1, wherein the molar ratio of alkanol to cyclic urea to a copper salt catalyst is 1:(0.4–0.5):(0.04–0.06).

* * * * *

UNITED STATES PATENT AND TRADEMARK OFFICE
CERTIFICATE OF CORRECTION

PATENT NO. : 5,151,541

DATED : September 29, 1992

INVENTOR(S) : Joerg et al.

It is certified that error appears in the above-identified patent and that said Letters Patent is hereby corrected as shown below:

Column 4, line 64, Claim 9, last line: after "1:(", delete the letter "b".

Signed and Sealed this

Twenty-first Day of September, 1993

Attest:

BRUCE LEHMAN

*Attesting Officer*  *Commissioner of Patents and Trademarks*